(12) United States Patent
Staub et al.

(10) Patent No.: US 9,616,454 B2
(45) Date of Patent: Apr. 11, 2017

(54) MULTICOMPONENT CARTRIDGE FOR SINGLE USE

(75) Inventors: Andreas Staub, Stadel (CH); Percy Leue, Singen (DE)

(73) Assignee: SULZER MIXPAC AG, Haag (CH)

( * ) Notice: Subject to any disclaimer, the term of this patent is extended or adjusted under 35 U.S.C. 154(b) by 1859 days.

(21) Appl. No.: 12/658,540

(22) Filed: Feb. 9, 2010

(65) Prior Publication Data

US 2010/0206904 A1 Aug. 19, 2010

(30) Foreign Application Priority Data

Feb. 13, 2009 (EP) ..................... 09152854

(51) Int. Cl.
| | | |
|---|---|---|
| B65D 81/32 | (2006.01) | |
| B05C 17/005 | (2006.01) | |
| A61C 5/06 | (2006.01) | |
| A61B 17/00 | (2006.01) | |
| B05C 17/01 | (2006.01) | |

(52) U.S. Cl.
CPC ........ B05C 17/00553 (2013.01); A61C 5/064 (2013.01); B05C 17/00559 (2013.01); *A61B 2017/00495* (2013.01); *B05C 17/00576* (2013.01); *B05C 17/0146* (2013.01)

(58) Field of Classification Search
CPC ........ B05C 17/00553; B05C 17/00559; B05C 17/00576; B05C 17/0146; A61C 5/064; A61B 2017/00495
USPC ..... 222/137, 145.5, 153.01, 145.6, 134, 139
See application file for complete search history.

(56) References Cited

U.S. PATENT DOCUMENTS

| | | | | |
|---|---|---|---|---|
| 3,730,394 | A * | 5/1973 | Woodson | 222/137 |
| 3,738,535 | A * | 6/1973 | Nicholls | 222/137 |
| 4,771,919 | A * | 9/1988 | Ernst | 222/134 |
| 6,612,465 | B2 * | 9/2003 | Pierson et al. | 222/82 |
| 7,207,607 | B2 * | 4/2007 | Brugner et al. | 285/401 |
| 7,306,121 | B2 * | 12/2007 | Ophardt et al. | 222/209 |
| 7,468,049 | B2 * | 12/2008 | Laveault | 604/82 |
| 7,748,567 | B2 * | 7/2010 | Horner et al. | 222/135 |
| 7,963,937 | B2 * | 6/2011 | Pauser et al. | 604/82 |
| 8,033,429 | B2 * | 10/2011 | Keller | 222/145.6 |
| 8,096,449 | B2 * | 1/2012 | Keller | 222/137 |
| 2004/0216591 | A1 * | 11/2004 | Assadi et al. | 89/1.14 |
| 2006/0054636 | A1 * | 3/2006 | Brennan et al. | 222/137 |

FOREIGN PATENT DOCUMENTS

| | | |
|---|---|---|
| DE | 203 16 879 U1 | 3/2005 |
| DE | 20 2008 007801 | 8/2008 |
| WO | WO 2005/118154 A1 | 12/2005 |
| WO | WO 2009/021033 A1 | 2/2009 |

\* cited by examiner

*Primary Examiner* — Charles P Cheyney
(74) *Attorney, Agent, or Firm* — Francis C. Hand; Carella, Byrne, et al.

(57) ABSTRACT

A multicomponent cartridge which is designed for single use includes two separate supply chambers arranged coaxially of each other and two pistons. The two pistons are movable via a plunger to simultaneously discharge two components. A guide element guides the two pistons in the respective supply chambers and contains a discharge opening for discharging the first component. The guide element is movable relative to a housing via a movement element in order to open the discharge opening.

8 Claims, 13 Drawing Sheets

MULTICOMPONENT CARTRIDGE FOR SINGLE USE

This invention relates to a multicomponent cartridge for single use which is suitable for the simultaneous discharge of two components which can be mixed prior to use.

Multicomponent cartridges are known from DE 20 2008 007 801 U1. However, a disadvantage of such known cartridges is that a large number of component parts have to be used. The multicomponent cartridge in accordance with the prior art is designed both for single use and also for multiple use. However, it has been shown that on a multiple use of such a multicomponent cartridge the mixing can be irregular and it can be difficult to seal such a multicomponent cartridge once it has been used for the first time. For this reason, multicomponent cartridges which have been used once can only be stored with limitations. The filling material comes into contact with air due to the deficient sealing and its properties can thereby change, i.e. it can, for example, cure.

A multicomponent cartridge of coaxial design which is also shown in DE 20 2008 007 801 U1 can have fewer sealing problems; however, the problem of non-uniform mixing remains. The non-uniform mixing has the consequence that on re-use of the multicomponent cartridge in each case when the multicomponent cartridge is used, the result of the mixing is different; this means that a constant quality of the filling material cannot be achieved.

Accordingly, it is an object of the invention to develop a multicomponent cartridge which has a simple construction and is exclusively designed for single use.

A further object of the invention is to prevent an unintended movement of the piston by accidental actuation of the plunger.

A further object of the invention is to indicate visually to the user whether a filled multicomponent cartridge is intact.

Briefly, the invention provides a multicomponent cartridge which includes a first supply chamber for a first component and a second supply chamber for a second component. In the storage state, the first component is separate from the second component. The first supply chamber is coaxially arranged around the second supply chamber and forms a ring or annular space, with a first piston being movably arranged in the first supply chamber and a second piston being movably arranged in the second supply chamber. The first and second pistons are movable by means of a plunger to simultaneously discharge the two components.

In addition, a guide element is provided to guide the first piston in the first supply chamber and to guide the second piston in the second supply chamber. The guide element contains a discharge opening through which the first component can be discharged out of the first supply chamber. The guide element is arranged in a housing, with the guide element being movable relative to the housing by means of a movement element, whereby the discharge opening can be freed.

The operational concept of the multicomponent cartridge of the invention thus fundamentally differs from the prior art. The user who requires a certain amount of filling material takes a multicomponent cartridge to hand as previously described. First of all, the user ensures that the multicomponent cartridge is intact. For this purpose, the user moves the movement element in the manner shown on the housing of the cartridge. If this movement of the movement element cannot be carried out, the user knows that the multicomponent cartridge has already been opened.

If the user can operate the movement element in the intended manner, the user thus opens the discharge openings so that the filling material can pass through the discharge openings and be guided to the mixer. The user can adjust the multicomponent cartridge according to personal requirements to guide the filling material to the desired place. For this purpose, the user can also install the multicomponent cartridge into a commercially available discharge apparatus. The discharge apparatus includes a pressure means which exerts a pressure on the plunger of the multicomponent cartridge which sets the pistons in motion in their supply chambers, whereby the filling material is displaced out of the corresponding supply chambers. The filling material arrives at the mixer via the discharge openings, is mixed and is discharged at the end of the mixer. The end of the mixer can contain suitable elements for positioning the jet of the mixture of the components of the filling material.

Advantageously, the guide element includes the mixer, in particular a static mixer. The position of the guide element relative to the mixer is predetermined by this measure. However, this means that it can be expected for all multicomponent cartridges of this design that the mixing is of the same quality. The guide element also contains the discharge openings so that the fluid flow of the components is the same for each individual multicomponent cartridge. Thus, surprisingly, an improved reproducibility in relation to the achieved mixing can be achieved with the concept in accordance with the invention, although a separate multicomponent cartridge is required for each application. Moreover, through this solution, a smaller number of individual parts result so that the assembly of the multicomponent cartridge can take place very easily.

No complicated mounting steps are thus required for the filling and the assembly of the multicomponent cartridge. It results from this that the filling can take place shortly before the designated use, as the filling can take place decentrally at different places. This advantage becomes even more important when the filling material only has a very limited shelf life.

The movement element includes an external thread provided at the guide element into which an internal thread provided at the housing can engage. This embodiment of the movement element as a rotary element is preferred as it is easy to handle and as a defined angle of rotation can be associated with a defined gap width between the first end region of the guide element and the housing.

In accordance with a second embodiment, the piston and the plunger can be formed from one piece. This one-piece design is advantageous as, besides the reduction of the number of components and the associated simplification of the multicomponent cartridge, a mis-positioning of one of the pistons and thus a slanted positioning of the pistons can also be completely excluded. The piston part of the plunger can consequently also have a smaller installation height. The piston part is thus guided by the connecting element of a housing element so that a canting of the piston part can be avoided in accordance with this embodiment.

Preferably, the plunger can be connected to the housing element in one piece. The housing element with the plunger is placed onto the pistons and is connected to the guide element after the filling of the supply chambers with the corresponding components and the insertion of the first and second pistons. For this purpose, an engagement element is provided at the housing element which is brought into engagement with a spring element at the guide element. The housing element is thus rotationally fixedly connected to the guide element. The plunger connected to the housing element holds the pistons in their starting position so that the filling material in the supply chambers is locked in. The filled multicomponent cartridges can be stored in this state; in the following, this state will be known as a storage state. When the plunger, the pistons and the housing element form a unit, this unit will be connected to the guide element after filling.

The housing element has a predetermined breaking point via which the plunger is connected to the housing element in the storage state. The predetermined breaking point can act as a seal to maintain the inner space of the housing element free from contaminants. In accordance with a further embodiment, the predetermined breaking points include ribs or webs which run in the longitudinal direction in relation to the plunger axis. Furthermore, this allows the user to evaluate whether the multicomponent cartridge is intact. If the predetermined breaking point is intact, then on discharge, an increased resistance has to be overcome at the beginning of the discharge process which is caused by the fact that an increased application of force is required to break through the predetermined breaking point. The break through of the predetermined breaking point is visible by the initiated displacement of the plunger relative to the housing element and is audible in most cases.

The plunger is then movable relative to the housing element when a force is applied to the plunger when a discharge of the first and second components should occur, with the connection between the housing element and the plunger being interrupted.

The guide element is connectable to a housing element via the engagement element. The use of the engagement element allows a simple and unproblematic assembly of the multicomponent cartridge after the filling of the supply chambers. In particular, the engagement element can include a spring element, with the spring element being able to be formed as a projection at the perimeter of the guide element. The spring element engages into a recess of the housing element so that the housing element is rotationally fixedly connected to the guide element.

The first piston includes a ring piston which has a ring shaped seal at its outer piston skirt. The first supply chamber is arranged coaxially to the second supply chamber as this arrangement is space-saving and a small construction volume of the multicomponent cartridge is achieved. Since the first supply chamber is ring shaped, the first piston is formed as a ring piston. Naturally, the first supply chamber could also have an angled cross-section. The first piston can still be ring shaped, however, its shape is no longer circular ring shaped.

The second piston preferably has a vent element in the region of the predetermined breaking point as, on the insertion of the piston after the filling of the supply chambers with the corresponding components, air can remain between the filling material and the piston, which can disadvantageously influence the discharge process. Alternatively or in addition thereto, the guide element can also include a vent element.

The plunger and the piston can be at least partially hollow. The material consumption for the plunger and the pistons is hereby decreased. Furthermore, the plunger and pistons can be produced simpler in an injection molding process when material accumulation can be avoided and thin walled components can be used. Each of the components which can form the multicomponent cartridge can be at least partially composed of foamed plastic.

The use of a one-piece piston which simultaneously acts as a plunger has the following advantages:

The multicomponent cartridge can be installed in a standard discharge apparatus which is widely distributed on the market. Thus, the end user does not have to purchase an additional discharge apparatus, but can rather use the multicomponent cartridge with a standard discharge apparatus.

The plunger forms the connection to the standard discharge apparatus. This plunger can have dimensions suitable for the standard discharge apparatus.

The multicomponent cartridge can only be employed for a single use and is not suitable for a plurality of uses. The static mixer is therefore also not exchangeable.

The multicomponent cartridge can be designed as a slim and narrow construction. The multicomponent cartridge can therefore be easily stored and transported.

It is possible to fill the multicomponent cartridge just before use. The empty multicomponent cartridges can therefore be stored without any concern and the filling material can be stored more simply in suitable containers separate from the cartridges.

Furthermore, the multicomponent cartridges and/or their individual parts can be transported more easily and more cost effectively in the empty state.

Furthermore, the multicomponent cartridge can include a protection against accidental opening. For this purpose, the plunger can be fixedly connected to the surrounding housing. Only on the discharge is the connection between the plunger and the housing interrupted by the pressure applied to the plunger. Thus, it is visible at any time whether the multicomponent cartridge is still new or has already been used, i.e. is no longer intact. Furthermore, on separating the connection between the housing and the plunger, a sound arises so that it is also acoustically detectable whether the multicomponent cartridge was intact prior to use, i.e. new. A non-authorized refilling or reuse can be avoided in a simple manner.

The concept in accordance with the invention has fewer individual parts than the prior art. For example, because the mixer is fixedly connected to the housing of the cartridge, the incoming flow to the mixer is the same during the whole discharge cycle. It does not only follow from this that the mixing quality of one and the same multicomponent is essentially the same for the total discharge cycle, but rather there are also less differences in the mixing quality with different multicomponent cartridges of the same type.

In the following the invention will be described with reference to the drawings. There are shown.

Figure 1:
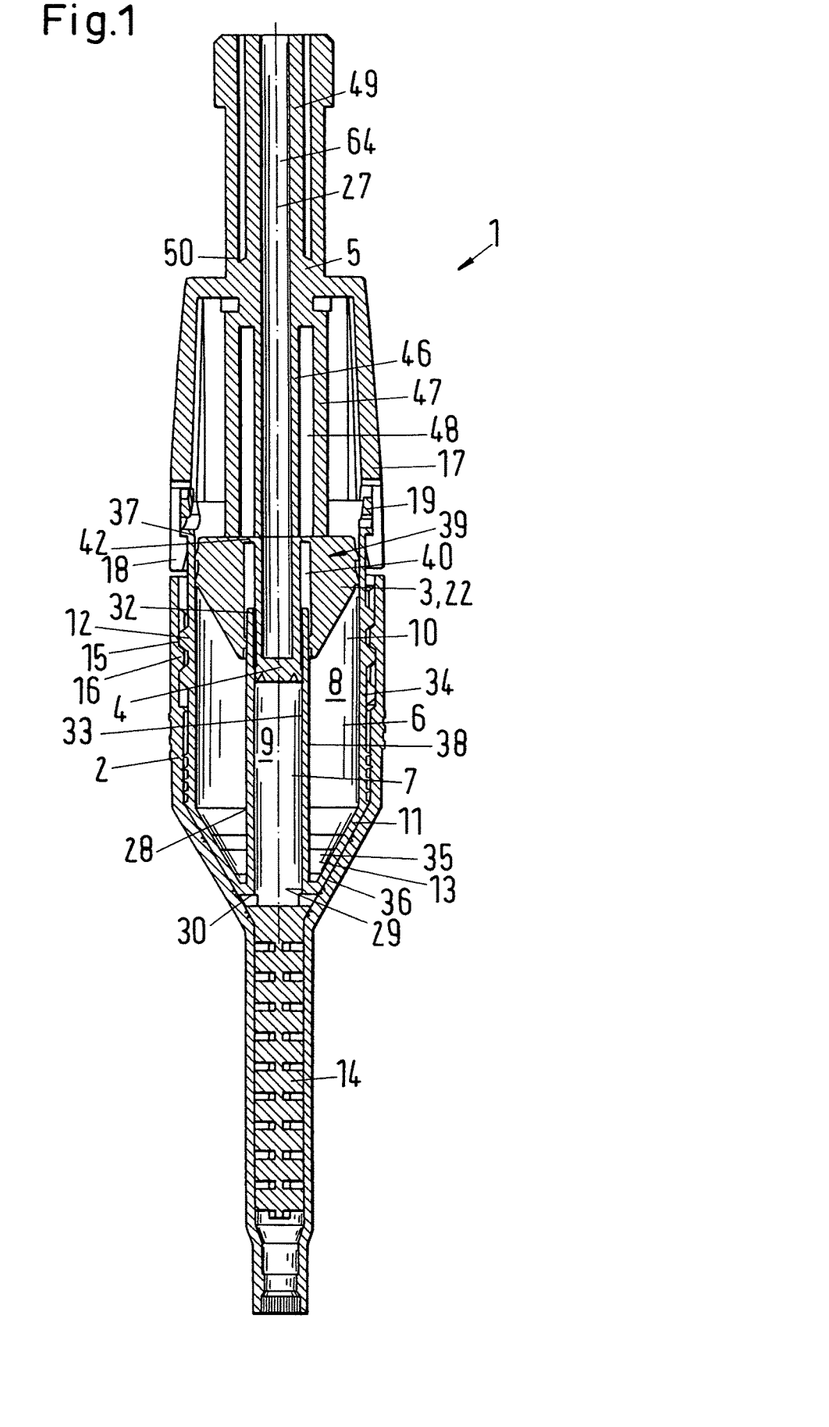
FIG. 1 illustrates a cross-sectional view of a multicomponent cartridge in accordance with a first embodiment of the invention.

Referring to FIG. 1, the multicomponent cartridge 1 is designed for single use. In particular, such a multicomponent cartridge is used for the dispensing of small and very small amounts of filling material.

The multicomponent cartridge 1 includes a first supply chamber 6 for a first component 8 and a second supply chamber 7 for a second component 9. The first supply chamber 6 is separate from the second supply chamber 7 so that the two components do not come into contact with one another. Such components usually react with one another as soon as they come into contact with one another, with chemical reactions being able to take place. The interaction of the components is usually the effect which is required in an application; however, this interaction is unwanted as long as the components are not being used in the scope of their determined application. Thus, prior to use, the multicomponent cartridge 1 has to be stored and transported and indeed from time to time in a filled state, which in the following will be described as the storage state. It has to be ensured for the complete duration of the storage state that the two components 8, 9 do not come into contact with one another.

The first supply chamber 6 is coaxially arranged around the second supply chamber 7 and forms a ring (or annular) space 10. The ring space 10 can be formed in a circular ring shape. The first supply chamber 6 is separated from the second supply chamber 7 by a dividing wall 28 so that the two components 8, 9 can be stored separately from one another. In this embodiment, the second supply chamber 7 extends along a longitudinal axis which coincides with the longitudinal axis 27 of the multicomponent cartridge.

The dividing wall 28 forms the outer boundary of the second supply chamber 7 and surrounds the supply chamber 7 as a skirt. The dividing wall 28 opens at a first end 30 into a second discharge opening 29. The second component 9 can be guided to a mixer 14 through the second discharge opening 29, see also FIG. 3. A plurality of second discharge openings 29 can also be provided between which webs 31 can be arranged which form the connection to the mixer 14.

The dividing wall 28 is a part of a guide element 11. The dividing wall 28 has a second end 32 which serves for the reception of a second piston 4. The second piston 4 is movably arranged in the second supply chamber 7. This second piston 4 glides along an inner side 33 of the dividing wall 28 of the guide element 11 in the direction of the first end 30 when the filling material in the second supply chamber 7, i.e. the second component 9, should be discharged. The guide element 11 is provided to guide the second piston 4 in the second supply chamber 7.

A first piston 3 is movably arranged in the first supply chamber 6. The guide element 11 is provided to guide the first piston 3 in the first supply chamber 6. The first supply chamber 6 is bounded at its inner side by the dividing wall 28 and is surrounded at its outer side by a skirt element 34 of the guide element 11. The skirt element 34 opens at a first end region 35 into a first discharge opening 13. The first component 8 can be guided to the mixer 14 through the discharge opening 13, see also FIG. 3 or FIG. 6. A plurality of first discharge openings 13 can also be provided between which connection webs 36 are arranged which form the connection to the dividing wall 28 or to the mixer 14.

The skirt element 34 is a part of the guide element 11. The dividing wall 28 and the skirt element 34 have an end region 35 which serves for the reception of the first piston 3. In the first supply chamber 6, the first piston 3 is movably arranged between the skirt element 34 and the outer side 38 of the dividing wall 28. This first piston 3 glides along the outer side 38 of the dividing wall 28 of the guide element 11 in the direction of the end region 35 when the filling material in the first supply chamber 6, i.e. the first component 8, should be discharged. The guide element 11 is provided to guide the first piston 3 in the first supply chamber 6.

The guide element 11 includes the mixer 14, which is, in particular, formed as a static mixer. In particular, the guide element 11 and the mixer 14 are designed as a single component.

Figure 4:
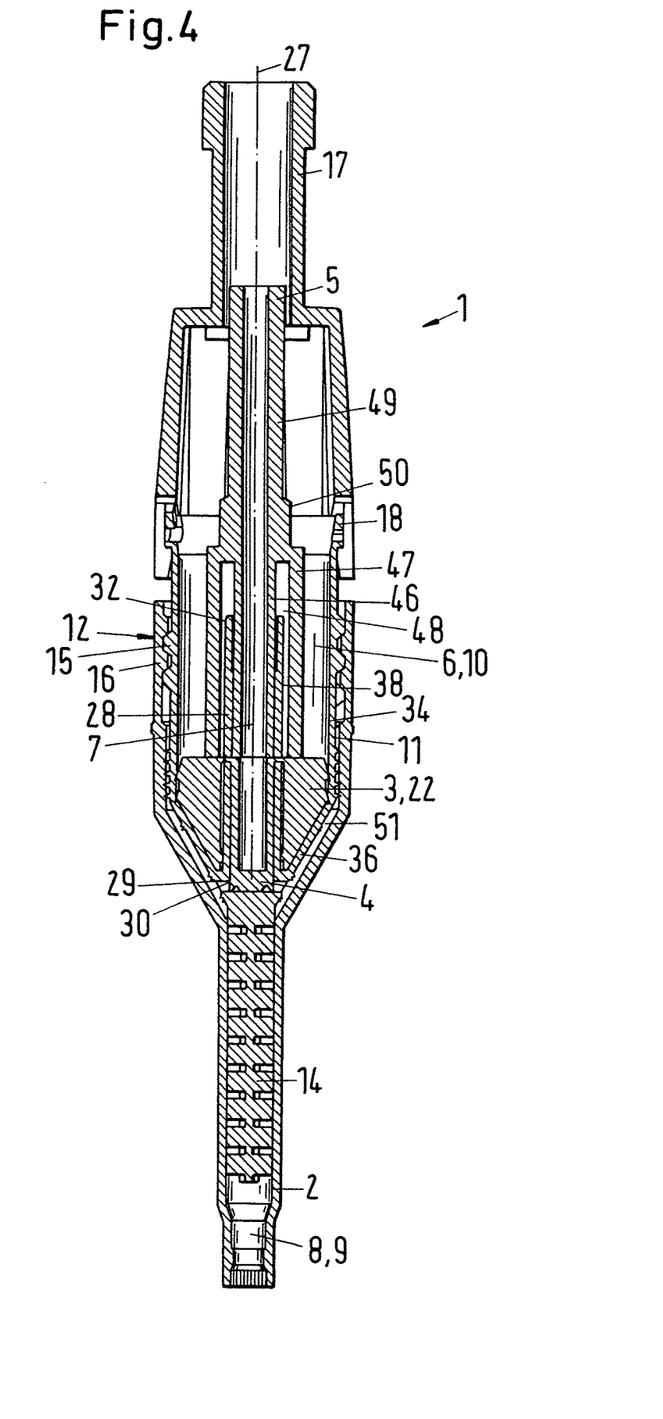
FIG. 4 illustrates a cross-sectional view of the multicomponent cartridge of FIG. 1 in the discharge position.

The first and second pistons 3, 4 are movable by means of a plunger 5 to simultaneously discharge the two components 8, 9. The plunger 5 is, in particular, adapted to lie on the first piston 3 and on the second piston 4. The plunger 5 is connected in one piece to the housing element 17 as long as the multicomponent cartridge is in the storage state. The housing element 17 has a predetermined breaking point 50 via which the plunger 5 is connected to the housing element 17 in the storage state. This predetermined breaking point 50 is severed at the beginning of the discharge of the filling material, as is shown in FIG. 4.

The plunger 5 contains two concentric plunger bodies 46, 47, an inner plunger body 46 and an outer plunger body 47. The inner plunger body 46 lies on the second piston 4, the outer plunger body 47 lies on the first piston 3. A ring shaped recess 48 is arranged between the inner plunger body and the outer plunger body and serves for the reception of the dividing wall 28 when the filling material is discharged from the first and second supply chambers 6, 7. The inner plunger body 46 and the outer plunger body 47 are connected to one another so that they move simultaneously during the discharge process to displace the pistons 3, 4 in the corresponding supply chambers 6, 7.

A connection element 49 forms the end of the plunger 5 and is adapted such that it can be fitted into a commercially available discharge apparatus. The connection element 49 is also arranged within the housing element 17. The connection element 49 can include a cavity which serves to save material.

The guide element 11 is connectable to a housing element 17 by means of an engagement element 18.

Figure 2:
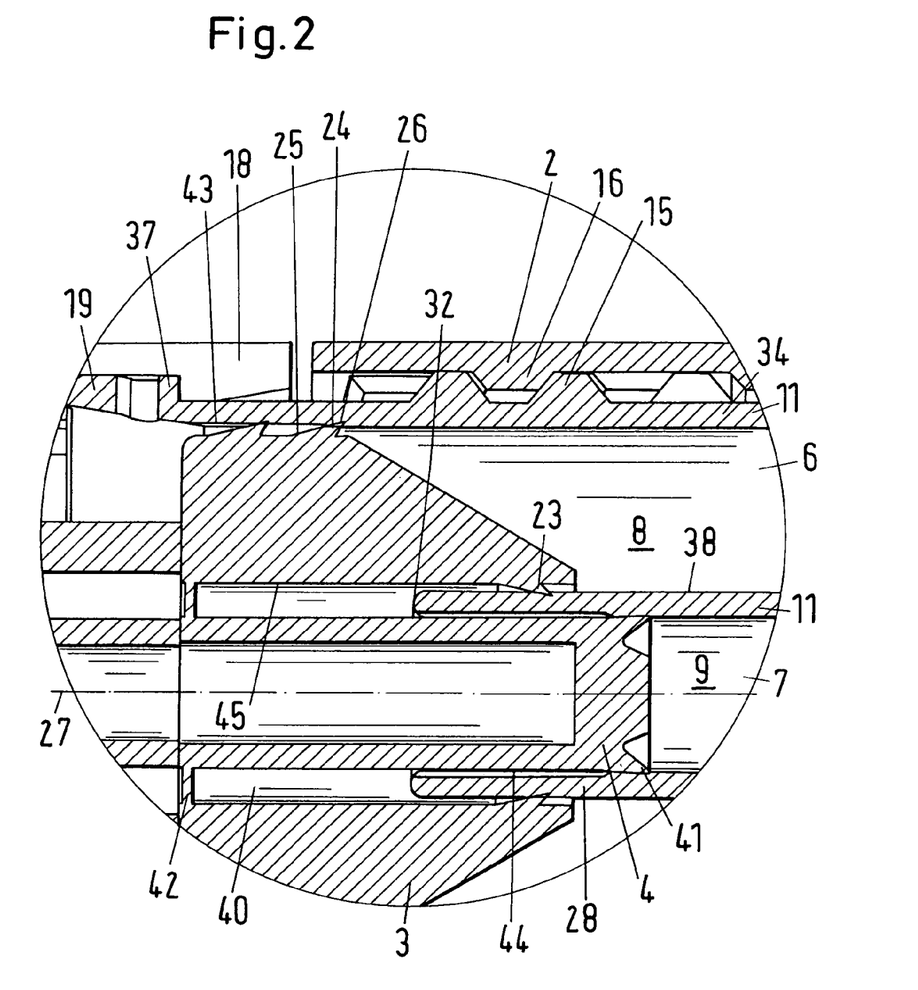
FIG. 2 illustrates a cross-sectional detail view of the piston of the multicomponent cartridge in accordance with FIG. 1.

The first and the second pistons 3, 4 can be connected to one another as is shown in FIG. 2. In particular, they can be designed as a single piston component 39. The piston component 39 has an annular slit 40 which serves for the reception of the dividing wall 28 of the guide element 11. The piston 4 adjoins at the inner side of the slit 40. The piston 4 has at least one sealing element 41 which is in particular made as a sealing lip. An advantage of the use of a piston component 39 lies in the fact that the piston component can be guided in a tilt safe manner. On the one hand, the second end 32 of the dividing wall 28 engages into the slit 40 and, on the other hand, the outer piston skirt 25 is guided along the skirt 34 of the guide element 11. The outer piston skirt 25 has a ring shaped seal 24; the inner piston skirt 45 also has at least one ring shaped seal 23.

The slit 40 is in particular ring shaped and has a bridging element 42 at the slit base which represents the connection between the piston 3 and the piston 4 of the piston component 39. If the piston component 39 is moved in the direction of the discharge opening 30 to discharge the filling material, i.e. moved to the right in FIG. 2, then the bridging element 42 is severed when it is incident on the second end 32 of the dividing wall 28. Subsequently, the piston 4 and the piston 3, which is adapted as a ring piston 22, move parallel to one another but completely separate from one another due to the dividing wall 28. The ring shaped seal 23, 24 can include a vent element 26. Alternatively hereto, a vent element 43, 44 can be affixed at the guide element 11 in particular, at the skirt element 34 and/or at the dividing wall 28. The vent element 43 is preferably affixed in the vicinity of the second end region 37 of the skirt element 34. The vent element 44 is preferably affixed in the vicinity of the second end 32 of the dividing wall 28.

Figure 3:
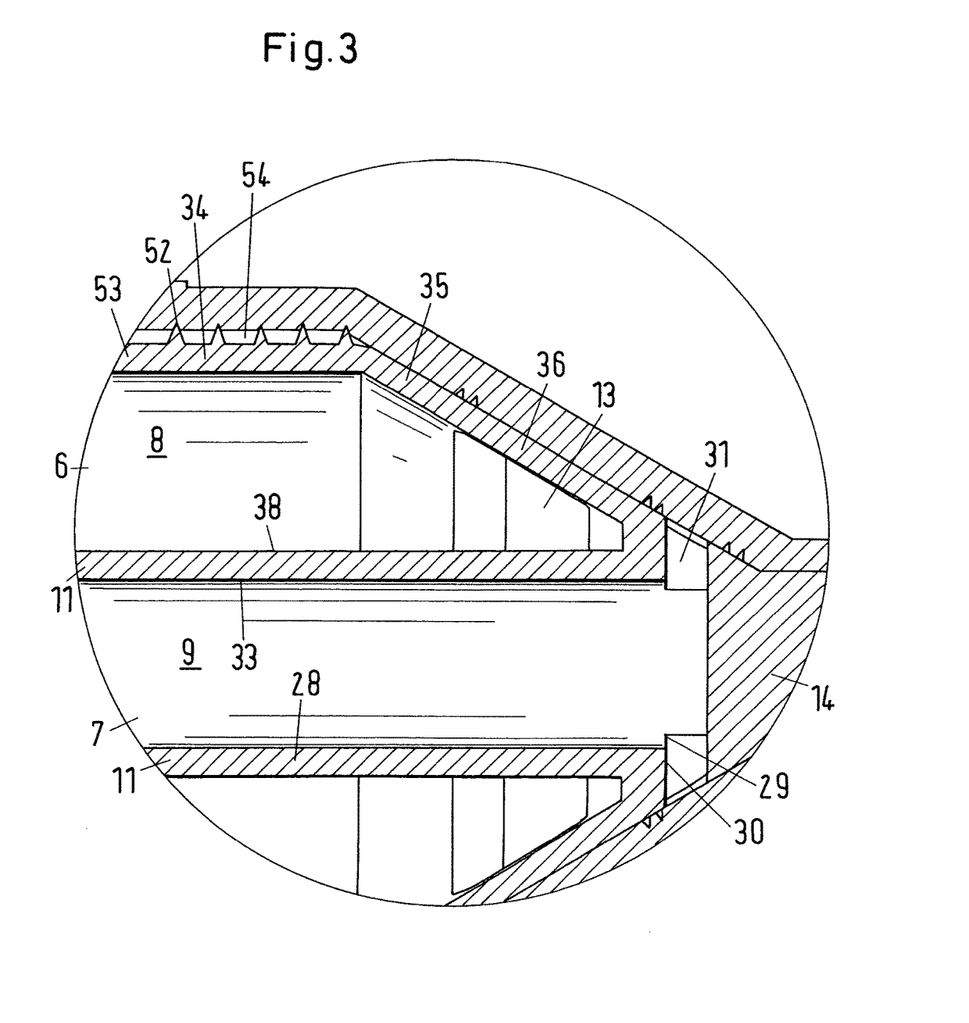
FIG. 3 illustrates a cross-sectional detail view of the multicomponent cartridge of FIG. 1 in the region of the first discharge opening.

FIG. 3 shows a detail of the multicomponent cartridge which includes the region of the first and second discharge openings 13, 29. The guide element 11 contains a discharge element 13 through which the first component 8 can be discharged out of the first supply chamber 6 and the guide element 11 is arranged in a housing 2, with the guide element 11 being movable relative to the housing 2 by means of a movement element 12 whereby the discharge opening 13 can be freed. The movement element 12 allows a relative movement of the housing 2 and the guide element 11.

The movement element 12 in accordance with a preferred variant which is shown in FIG. 2 includes an external thread 15 provided at the guide element 11 into which an inner thread 16 provided at the housing 2 can engage. By actuation of the movement element 12, i.e. by turning the housing 2 relative to the guide element 11, the guide element is displaced relative to the housing such that the first end region 35 of the skirt element 34 forms a spacing 51 (see FIG. 5) to the housing 2. The first discharge opening 13 is thus opened, this means that the component 8 of the filling material in the first supply chamber 6 can be discharged through the first discharge opening 13 and can be guided in the passage 51 (FIG. 5) formed between the housing 2 and the first end region 35 in the direction of the mixer 14. In the region of the second discharge opening 29, the first component 8 comes into contact with the second component 9 which, coming from the second supply chamber 7, is discharged through the discharge opening 29. This state is also illustrated in FIG. 5.

FIG. 4 shows the multicomponent cartridge in accordance with FIG. 1 at the end of the discharge of the filling material from the first and second supply chambers 6, 7. The plunger 5 is moved relative to the housing element 17 when a force is applied to the plunger 5. This force can be applied by a commercially available discharge apparatus or also manually. The connection between the housing element 17 and the plunger 5 which is formed as a predetermined breaking point 50 (i.e. a frangible connection) is severed when a pressure force is applied to the connection element 49.

Figure 5:
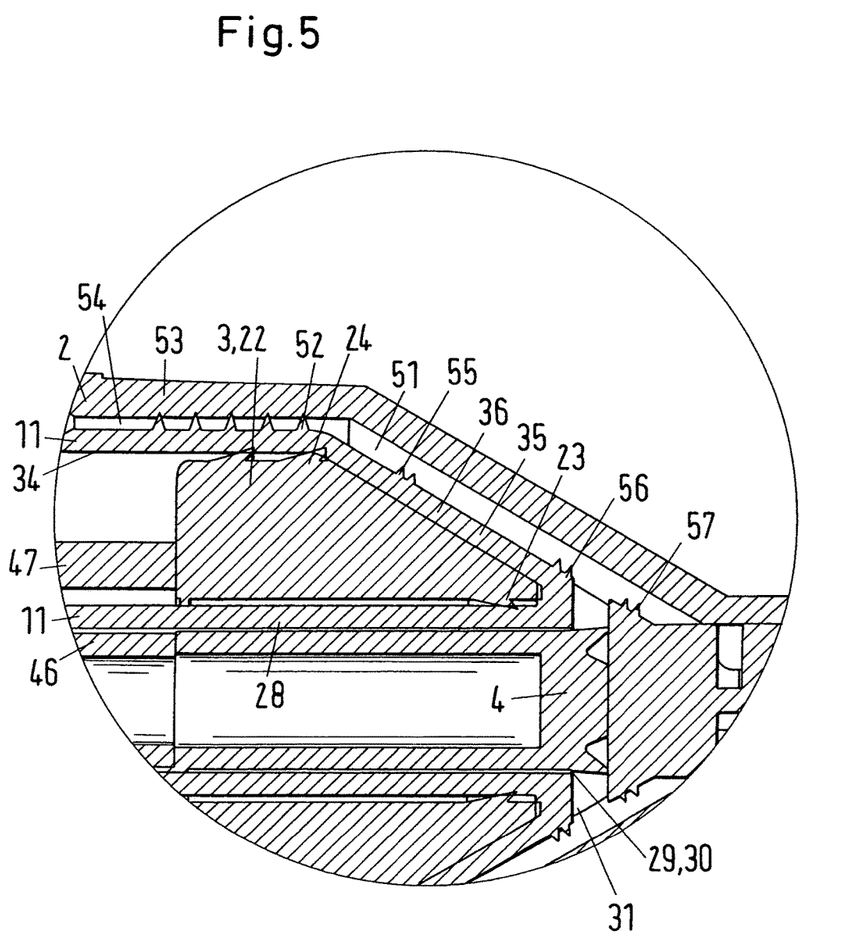
FIG. 5 illustrates a cross-sectional detail view of the multicomponent cartridge of FIG. 1 in the region of the first discharge opening in the discharge position.

FIG. 5 shows a detail of the multicomponent cartridge in accordance with FIG. 1 in the region of the first discharge opening 13 in the discharge position. FIG. 5 thus shows the positioning of the guide element 11 relative to the housing 2 when the filling material has been discharged from the first and second supply chambers 6, 7 via the mixer 14, i.e. when the discharge is finished. The filling material is thus being used as intended as the mixture of the first component 8 and the second component 9 leaving the mixer 14. Before the discharge can be started, i.e. the situation in accordance with FIG. 3 is present, the movement element 12 has to be actuated, as has already been described in connection with FIG. 2. The discharge opening 13 is opened by actuation of the movement element 12.

By turning the movement element 12, the passage 51 already mentioned in connection with FIG. 3 is formed between the guide element 11 and the housing 2, through which the first component 8 is guided to the mixer 14 through the discharge opening or a plurality of discharge openings 13. The discharge openings are applied in the conical wall of the first end region 35 of the guide element 11, with the section of FIG. 5 being chosen such that the connecting web 36 is shown which connects the dividing wall 28 of the guide element 11 to the skirt element 34 of the guide element 11.

The discharge opening 13 is closed in the representation in accordance with FIG. 5 by the ring piston 22 which forms the first piston 3. The discharge opening 29 is closed by the second piston 4. The first component 8 which is present in the passage 51 can now be guided in the direction of the mixer 14, as at least one sealing element 52 is arranged between the skirt element 34 of the guide element 11 and the housing 2. The skirt element 34 is preferably cylindrical and is arranged concentrically to the housing 2 which likewise has a cylindrical section 52. The width of the gap 54 existing between the skirt element 34 and the cylindrical section 52 is not changed by the displacement of the housing 2 relative to the guide element 11 so that the sealing of this gap 54 does not pose any particular problems.

Furthermore, FIG. 5 shows sealing elements 55, 56, 57 on the outer side of the second end region 36 of the skirt element 34. These sealing elements 55, 56, 57 play a role in the filling of the first and second supply chambers 6, 7 with the corresponding first and second components 8, 9. When the supply chambers 6, 7 are filled, the guide element 11 abuts the inner wall of the housing 2. The gap 51 ideally has a zero gap width. Due to manufacturing tolerances, the gap width can locally be greater than zero, the sealing elements 55 and 56 are therefore provided to prevent that a first component 8 situated in the discharge opening 13 can move into such a narrow gap. The sealing elements 56 and 57 prevent the second component 9 from moving into a narrow gap 51 via the discharge opening 29. It is thus avoided by the sealing elements that the first and second components move into the gap and come into contact there in an undesired way.

Figure 6:
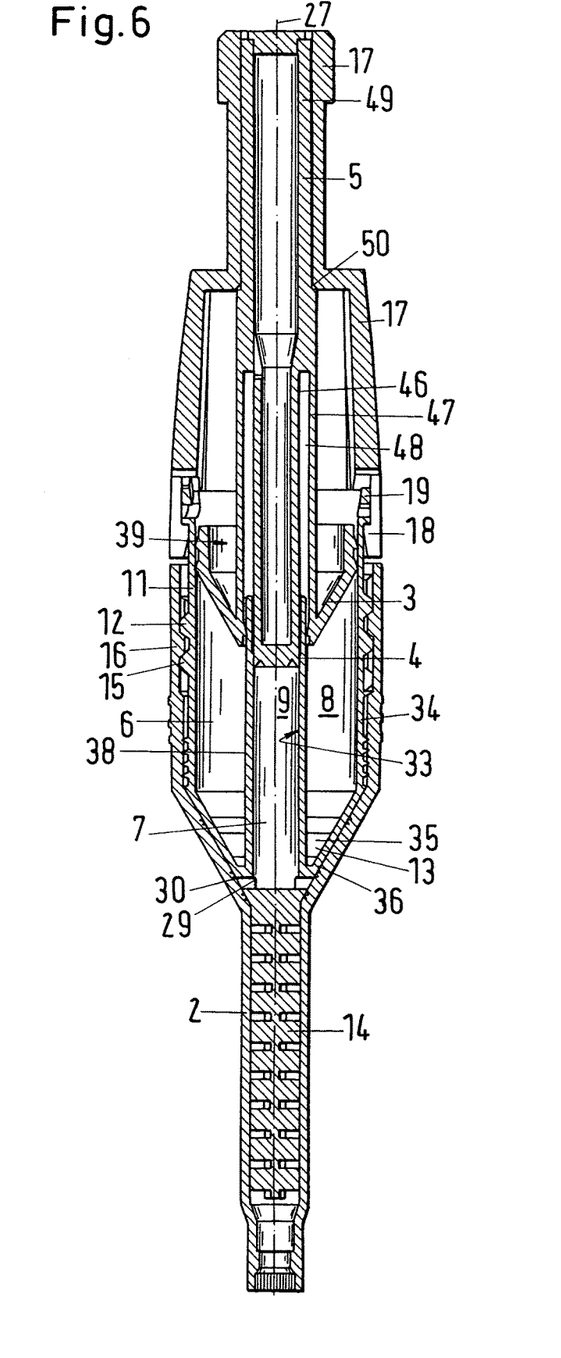
FIG. 6 illustrates a cross-sectional view of a multicomponent cartridge in accordance with a second embodiment of the invention.
Figure 7:
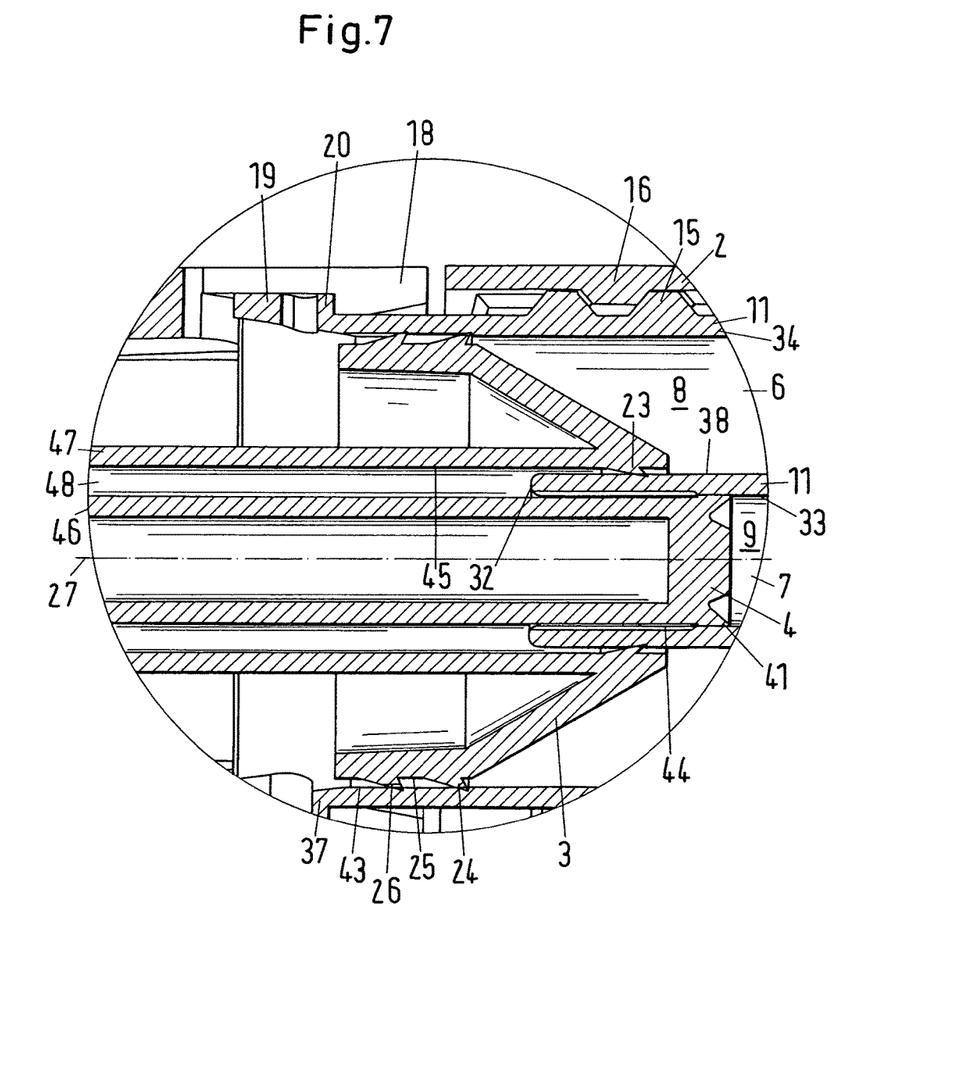
FIG. 7 illustrates a cross-sectional detail view of the piston of the multicomponent cartridge in accordance with FIG. 6.

Furthermore, as is shown in FIG. 5 and also FIG. 6 or FIG. 7, the guide element 11 is Connectable to a housing element 17 by means of an engagement element 18. The engagement element 18 includes a spring element 19. The spring element 19 is formed as a projection 20 at the perimeter of the housing 2. The spring element 19 engages into a recess (not shown) of the housing element 17 so that the housing element 17 is rotationally fixedly connected to the guide element 11.

Referring to FIG. 6, wherein like reference characters indicate like parts as above, in a second embodiment, the multicomponent cartridge has the first piston 3 and the plunger 5 made from one piece. The design and the mode of operation of this multicomponent cartridge do not otherwise differ from the first embodiment; thus reference is essentially made to the description of FIGS. 1 to 5 here.

A significant difference to the previous embodiment consists of the fact that the pistons 3, 4 are formed as one piece with the plunger 5. Since the plunger 5 is also connected to the housing element 17 in one piece, the number of components is reduced by at least one component compared to the previous embodiment. The pistons 3, 4 are at least partially hollow or thin-walled which, besides the reduced material consumption, can have advantages in the production of the pistons.

FIG. 7 shows a detail of the piston of the multicomponent cartridge in accordance with FIG. 6. FIG. 7 is the illustration corresponding to that of FIG. 2 in which the different configuration of the piston 3 can be seen. The piston 3 together with the piston 4 forms a piston component 39 and are separated from one another by a recess 48. The recess 48 serves for the reception of the dividing wall 28. Reference is made to FIG. 3 with respect to the illustration of the region of the discharge openings.

The vent element 43 is also shown in FIG. 7 as well as the vent element 44 at the inner side of the dividing wall 33. Preferably, the vent element has the shape of at least one groove shaped recess in the inner side of the dividing wall. A plurality of vent elements 44 arranged symmetrically to one another is particularly preferred, in FIG. 7 four vent elements 44 are arranged symmetrical to one another.

Figure 8:
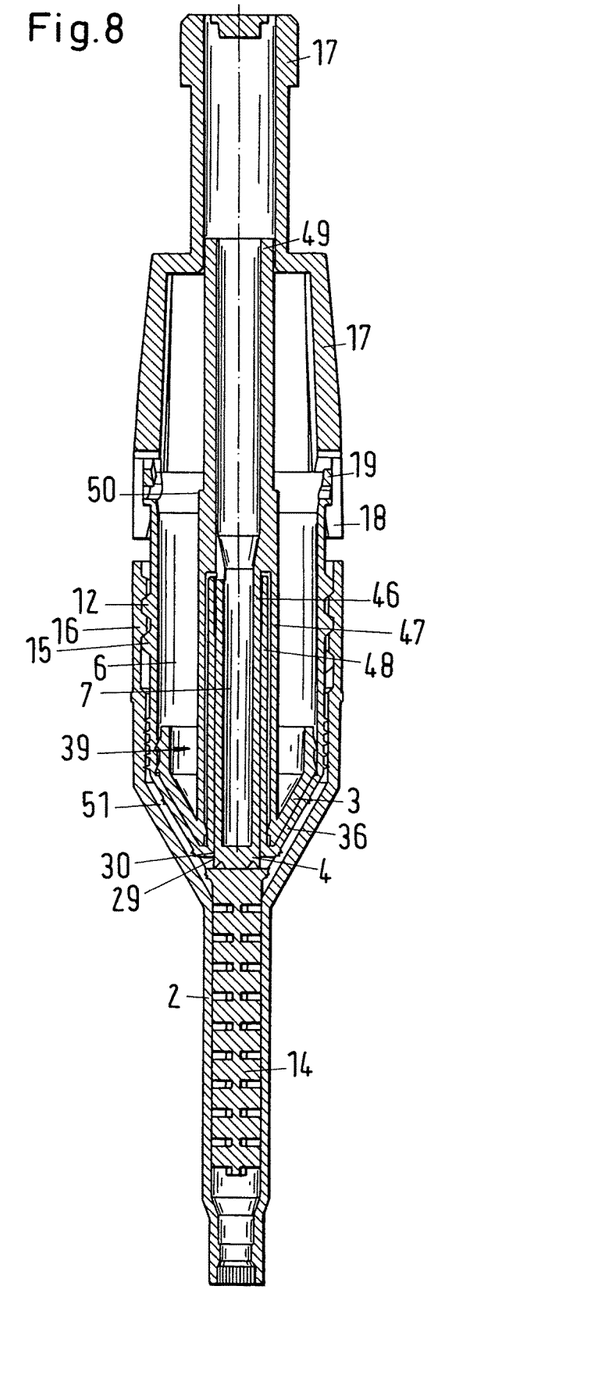
FIG. 8 illustrates a cross-sectional view of the multicomponent cartridge of FIG. 6 in the discharge position.

FIG. 8 shows the multicomponent cartridge in accordance with FIG. 6 in the discharge position. Reference is made to the description of FIG. 6.

Figure 9:
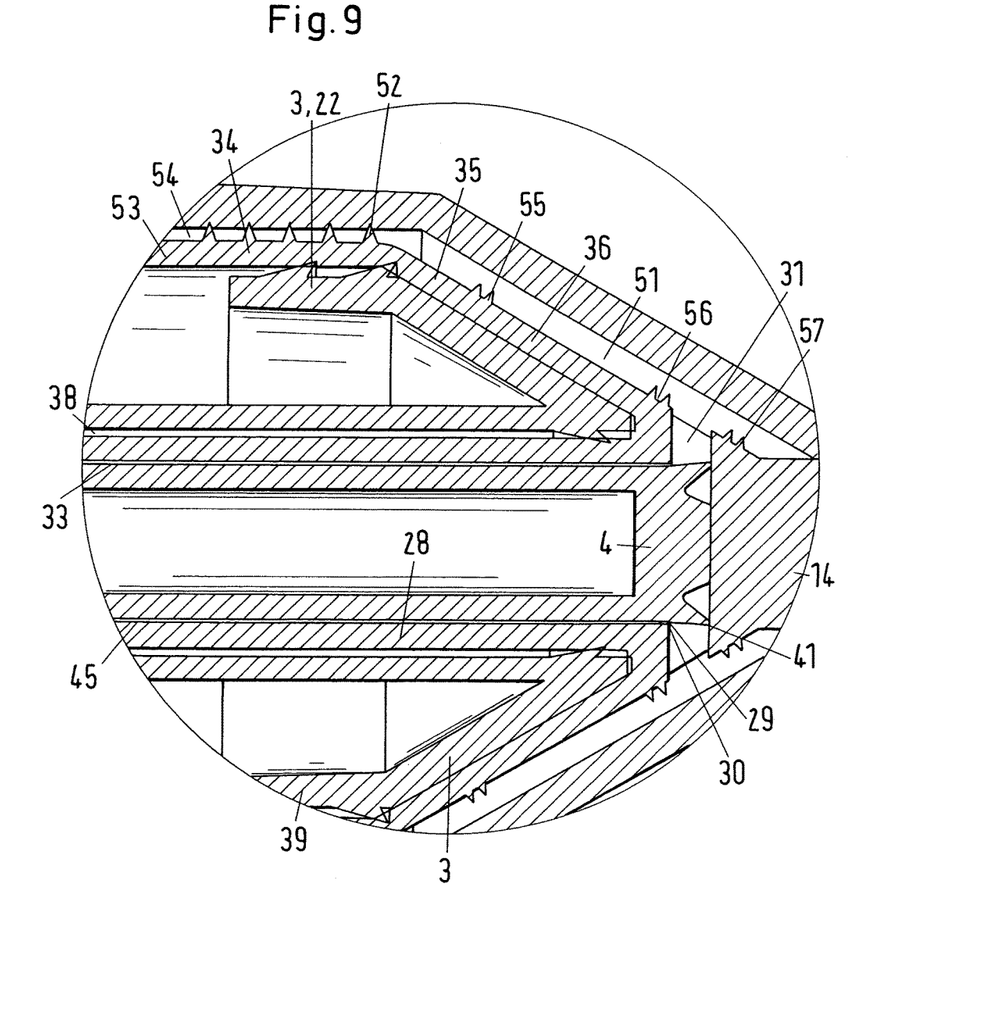
FIG. 9 illustrates a cross-sectional detail view of the multicomponent cartridge in accordance with FIG. 6 in the region of the discharge opening in the discharge position.

FIG. 9 shows a detail of the multicomponent cartridge in accordance with FIG. 6 in the region of the discharge opening in the discharge position. The mode of operation likewise corresponds to the mode of operation in accordance with FIG. 5 so that reference is made to the description there.

Figure 10:
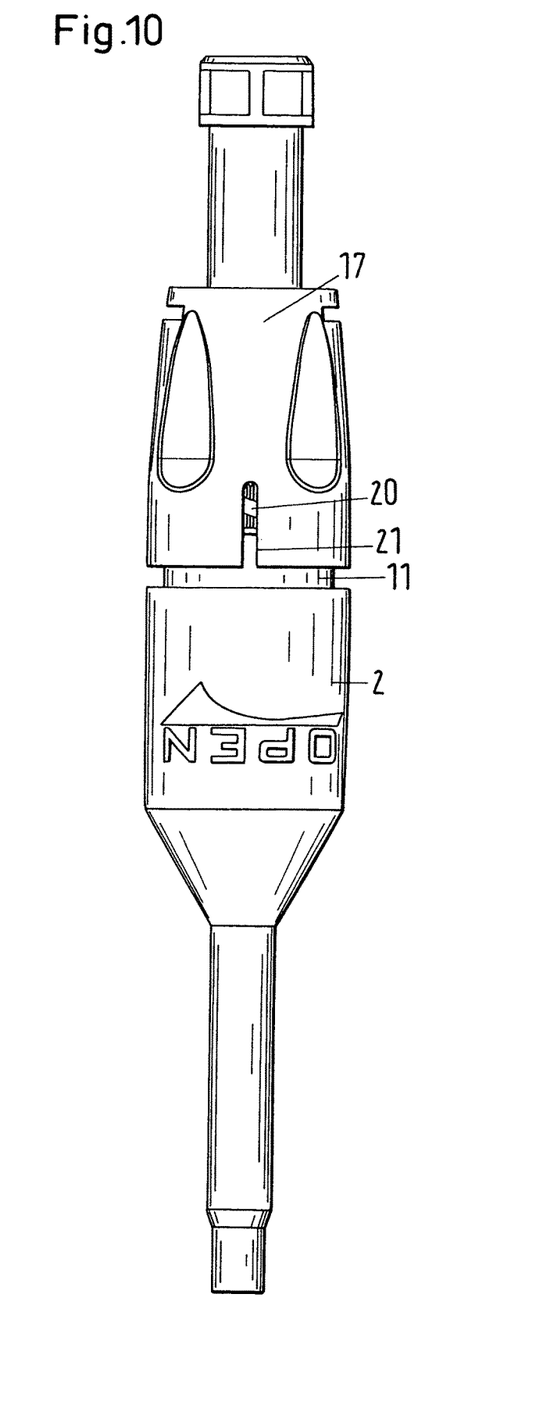
FIG. 10 illustrates an exterior view of the multicomponent cartridge of FIG. 1.

FIG. 10 shows the multicomponent cartridge in accordance with one of the previous embodiments in a view from outside. The guide element 11 is connectable to a housing element 17 by means of an engagement element 18. The engagement element 18 can include a spring element 19. The spring element 19 can be formed as a projection 20 at the perimeter of the guide element 11.

Figure 11:
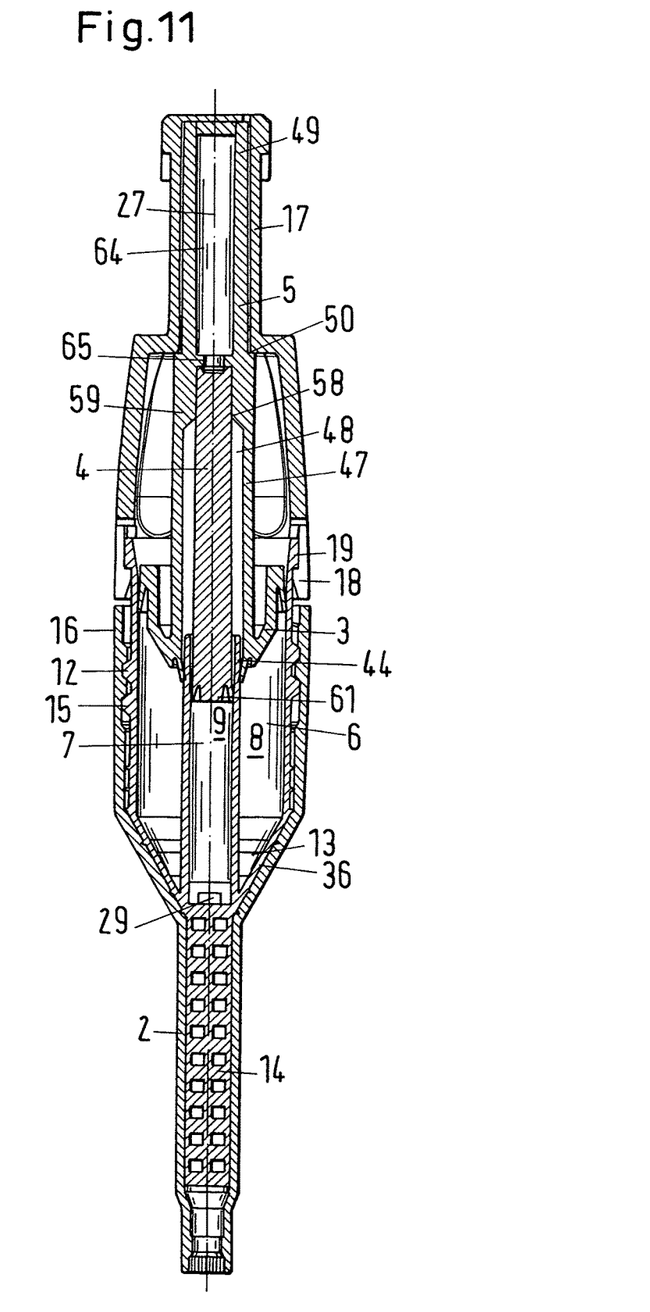
FIG. 11 illustrates a cross-sectional view of a multicomponent cartridge in accordance with a third embodiment of the invention.
Figure 12:
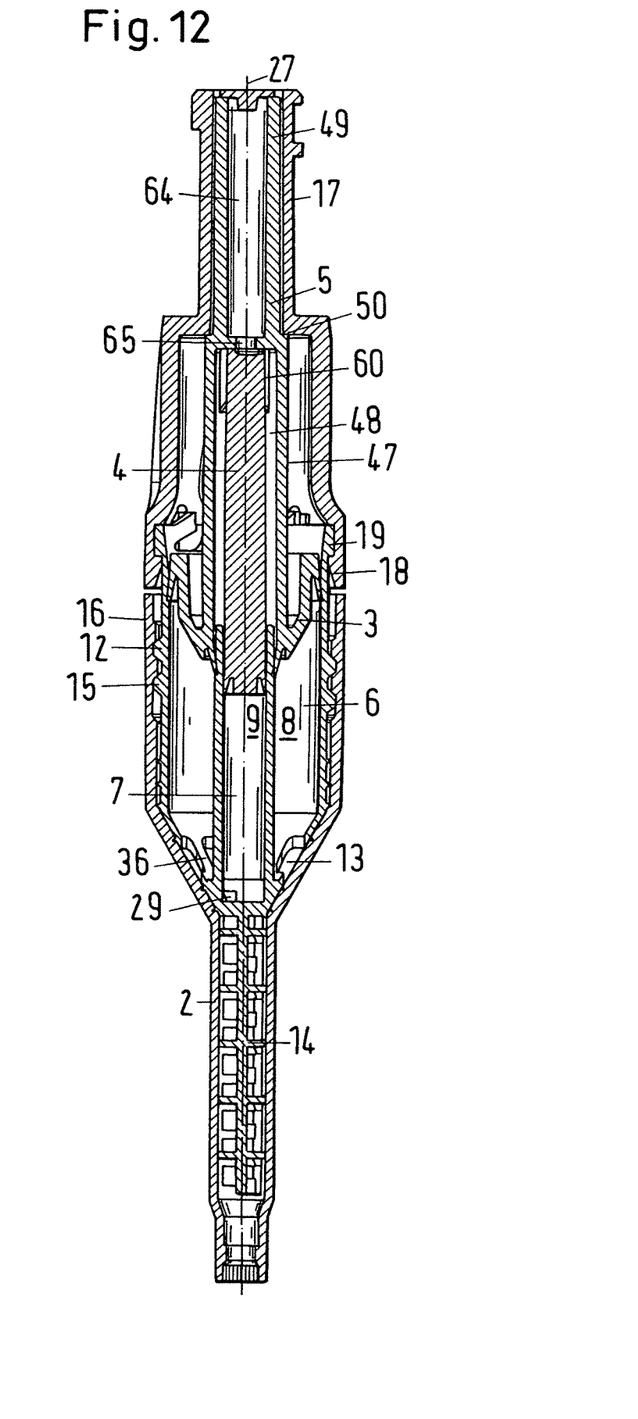
FIG. 12 illustrates a cross-sectional view of a multicomponent cartridge in accordance with a fourth embodiment of the invention.

FIG. 11 and FIG. 12 show a further variant of the multicomponent cartridge. Again, the same parts are provided with the same reference numerals so that reference is made to the corresponding description in the previous embodiments.

FIG. 11 thus shows a longitudinal section through the multicomponent cartridge. The first and second pistons 3, 4 are movable by means of a plunger 5 to simultaneously discharge the two components 8, 9. The plunger 5 is in particular carried out such that it is formed with the first piston in one piece and the second piston 4 is received in the plunger 5. The plunger 5 is connected to a housing element 17 in one piece as long as the multicomponent cartridge is in the storage state. The second piston 4 is held in the plunger 5 in particular by a plug connection assembly 58. Alternatively, a screwed connection or a snap on connection could also be provided for this purpose, i.e. a connection by means of which the second piston 4 is held in the plunger in a shape matched manner or force transmitting manner. In particular the plug connection assembly 58 includes at least one holding element 59, preferably a plurality of holding elements, which are formed as holding ribs. Particularly preferably, four holding ribs are provided by means of which the second piston 4 is held and centred. The inner edge or inner surface of the holding ribs can be adapted conically so that the second piston 4 can be fitted in. The second piston 4 simultaneously takes over the function of a plunger. The medial side first end 61 of the second piston 4 is guided in the dividing wall 28. As shown, the second piston 4 can be carried out as a solid body but can also be formed at least partially as a hollow body to save on weight and material.

FIG. 12 in this respect shows a longitudinal section which lies along a plane which is turned by 45° in relation to the sectional plane of FIG. 12 with respect to the longitudinal section of FIG. 11. It is shown in FIG. 12 that an intermediate space 60 lies between the holding elements 59 which is illustrated in FIG. 13 in more detail.

Figure 13:
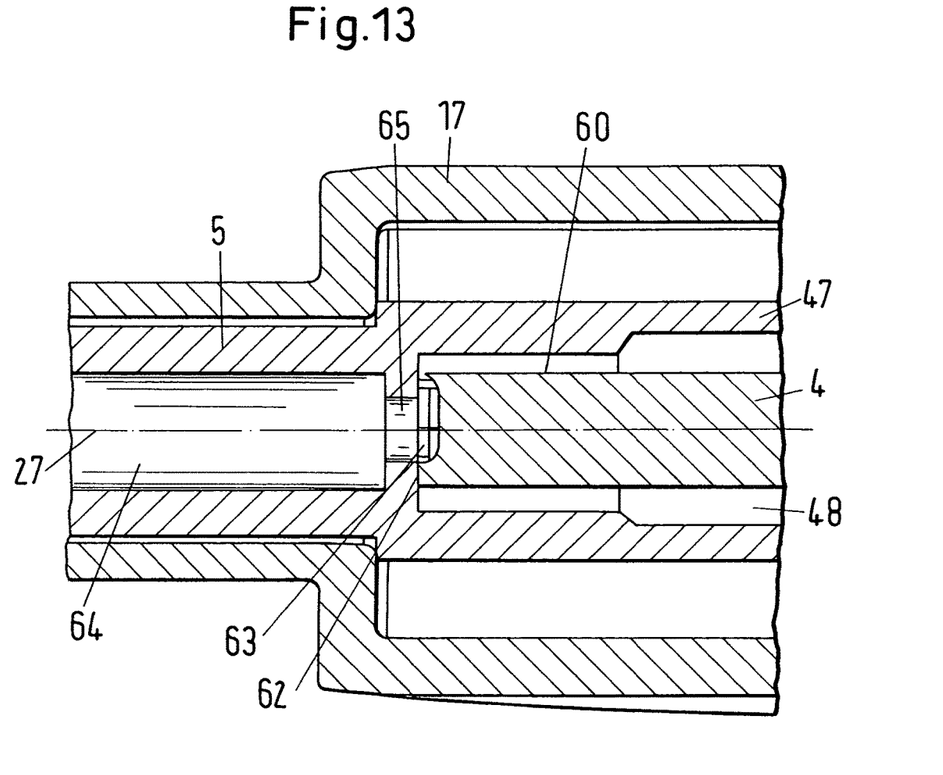
FIG. 13 illustrates a cross-sectional detail view of the piston of the multicomponent cartridge in accordance with each of FIGS. 11 and 12.

FIG. 13 shows a detailed view of the second end 62 of the second piston 4 opposite the medial side end 61. This second end 62 is held in the plunger 5 by the previously described plug connector assembly 58. The intermediate space 60, or each of the intermediate spaces when a plurality of intermediate spaces is provided, opens into a cut-out 63. Gas, in particular air can be guided out of the recess 48 through a bore 65 into a passage 64 in the interior of the plunger via the venting element 44 from the second supply chamber 7. The passage 64 can be open to the atmosphere as is shown in FIG. 1 or be provided with a closure element as is illustrated in FIG. 11 or FIG. 12. The recess 63 can include one or more grooves, in particular three grooves, which are arranged at an angle of 120° to one another. A venting of the recess 48 can thus take place by means of the cut-out or cut-outs 63 in connection with the intermediate spaces 60 which form the intermediate space between the outer plunger body 47 connected to the first piston 3 and the second piston 4.

What is claimed is:

1. A multicomponent cartridge comprising
a first supply chamber for a first component;
a second supply chamber separate from said first supply chamber for a second component and arranged coaxially within said first supply chamber:
a first piston movably arranged in said first supply chamber;
a second piston movably arranged in said second supply chamber;
a plunger for simultaneously moving said first piston and said second piston to simultaneously discharge the two components;
a guide element for guiding said first piston in said first supply chamber and for guiding said second piston in said second supply chamber, said guide element having a discharge opening for discharging the first component out of said first supply chamber,
a housing receiving said guide element;
a movement element for moving said guide element relative to said housing to form a gap between said housing and said guide element and to open said discharge opening for passage of the first component out of said first supply chamber into said gap; and
a housing element receiving said plunger and formed as one piece with said plunger.

2. A multicomponent cartridge in accordance with claim 1 further comprising a predetermined breaking point between said plunger and said housing element.

3. A multicomponent cartridge in accordance with claim 2 wherein said plunger is movable relative to said housing element in response to a force being applied to said plunger to break said breaking point when a discharge of the first component and the second component should be effected.

4. A multicomponent cartridge in accordance with claim 1 further comprising an engagement element connecting said guide element to said housing element.

5. A multicomponent cartridge in accordance with claim 4 wherein said engagement element includes a spring element.

6. A multicomponent cartridge in accordance with claim 5 wherein said spring element is formed as a projection at a perimeter of said guide element.

7. A multicomponent cartridge in accordance with claim 6 wherein said spring element engages into a recess in said housing element whereby said housing element is rotationally fixedly connected to said guide element.

8. A multicomponent cartridge comprising
a first supply chamber for a first component;
a second supply chamber separate from said first supply chamber for a second component and arranged coaxially within said first supply chamber:
a first piston movably arranged in said first supply chamber;
a second piston movably arranged in said second supply chamber;
a plunger for simultaneously moving said first piston and said second piston to simultaneously discharge the two components;
a guide element for guiding said first piston in said first supply chamber and for guiding said second piston in said second supply chamber, said guide element having a discharge opening for discharging the first component out of said first supply chamber,
a housing receiving said guide element;
a movement element for moving said guide element relative to said housing to form a gap between said housing and said guide element and to open said discharge opening for passage of the first component out of said first supply chamber into said gap; and
wherein said guide element includes a vent element.

* * * * *